United States Patent
Mohan et al.

(10) Patent No.: US 10,183,143 B2
(45) Date of Patent: Jan. 22, 2019

(54) OCCLUSION RESISTANT CATHETER AND METHOD OF USE

(71) Applicant: Bitol Designs, LLC, Alamo, CA (US)

(72) Inventors: Ashik A. Mohan, Alamo, CA (US); Avinash L. Mohan, Yorktown Heights, NY (US); Mark J. Bernhard, Alamo, CA (US)

(73) Assignee: Bitol Designs, LLC, Alamo, CA (US)

(*) Notice: Subject to any disclaimer, the term of this patent is extended or adjusted under 35 U.S.C. 154(b) by 489 days.

(21) Appl. No.: 14/216,530

(22) Filed: Mar. 17, 2014

(65) Prior Publication Data

US 2014/0288479 A1    Sep. 25, 2014

Related U.S. Application Data

(60) Provisional application No. 61/801,232, filed on Mar. 15, 2013.

(51) Int. Cl.
*A61M 25/00* (2006.01)
*A61M 27/00* (2006.01)

(52) U.S. Cl.
CPC ...... *A61M 25/0017* (2013.01); *A61M 27/006* (2013.01); *A61M 2025/0073* (2013.01)

(58) Field of Classification Search
CPC ...... A61M 2025/0073; A61M 25/0017; A61M 27/006
See application file for complete search history.

(56) References Cited

U.S. PATENT DOCUMENTS

| | | |
|---|---|---|
| 3,419,010 A | 12/1968 | Donald |
| 3,796,950 A | 3/1974 | Kuecken |
| 3,985,140 A | 10/1976 | Harris |
| 3,999,553 A | 12/1976 | Spitz et al. |
| D24,319 S | 1/1977 | Pemberton |
| D24,722 S | 2/1978 | Pemberton |
| D25,018 S | 11/1978 | Pemberton |
| 4,205,252 A | 5/1980 | Sinclair et al. |
| 4,260,983 A | 4/1981 | Falck et al. |
| 4,261,367 A | 4/1981 | Freese |

(Continued)

FOREIGN PATENT DOCUMENTS

| CN | 1056088 C | 9/2000 |
|---|---|---|
| WO | WO02/20083 A2 | 3/2002 |

*Primary Examiner* — Tatyana Zalukaeva
*Assistant Examiner* — Kai Weng
(74) *Attorney, Agent, or Firm* — Shay Glenn LLP

(57) ABSTRACT

An implantable occlusion and tissue ingrowth resistant fluid interface is provided with a housing, an orifice and a catheter port. The housing is formed from at least one biocompatible material and is configured without sharp edges or corners. The housing at least partially defines an internal housing cavity. The orifice member at least partially defines an orifice between the internal housing cavity and an exterior of the housing. The orifice has an elongated transverse cross-section configured with a length that is at least four times its maximum width. The catheter port is located on the housing and is configured to couple with a catheter such that the internal housing cavity is in fluid communication with a lumen of the catheter when the catheter is coupled to the catheter port. Embodiments having a moving cylinder, a rotor, and non-chemical surface modifications, as well as methods of use are also disclosed.

13 Claims, 15 Drawing Sheets

(56) References Cited

U.S. PATENT DOCUMENTS

| | | | |
|---|---|---|---|
| 4,271,840 A | 6/1981 | Lattin et al. |
| 4,327,251 A | 4/1982 | Fomenko et al. |
| 4,332,255 A | 6/1982 | Hakim et al. |
| 4,375,816 A | 3/1983 | Labianca |
| 4,399,437 A | 8/1983 | Falck et al. |
| 4,511,887 A | 4/1985 | Fiore |
| 4,540,400 A | 9/1985 | Hooven |
| 4,557,721 A | 12/1985 | Hooven |
| 4,576,589 A | 3/1986 | Kraus et al. |
| 4,578,057 A | 3/1986 | Sussman |
| 4,583,967 A | 4/1986 | Harris |
| 4,588,085 A | 5/1986 | Sussman |
| 4,598,579 A | 7/1986 | Cummings et al. |
| 4,601,724 A | 7/1986 | Hooven et al. |
| 4,605,395 A | 8/1986 | Rose et al. |
| 4,627,832 A | 12/1986 | Hooven et al. |
| 4,631,051 A | 12/1986 | Harris |
| 4,675,003 A | 6/1987 | Hooven |
| 4,676,772 A | 6/1987 | Hooven |
| 4,681,559 A | 7/1987 | Hooven |
| 4,705,499 A | 11/1987 | Hooven |
| 4,714,458 A | 12/1987 | Hooven |
| 4,714,459 A | 12/1987 | Hooven |
| 4,729,762 A | 3/1988 | Doumenis |
| 4,767,400 A | 8/1988 | Miller et al. |
| 4,769,002 A | 9/1988 | Hooven |
| 4,769,016 A | 9/1988 | Labianca |
| 4,776,838 A | 10/1988 | Sainte Rose et al. |
| 4,776,839 A | 10/1988 | Doumenis |
| 4,781,672 A | 11/1988 | Hooven |
| 4,950,232 A | 8/1990 | Ruzicka et al. |
| 5,069,663 A | 12/1991 | Sussman |
| 5,230,623 A | 7/1993 | Guthrie et al. |
| 5,336,166 A | 8/1994 | Sierra |
| 5,368,556 A | 11/1994 | Lecuyer |
| 5,409,462 A | 4/1995 | Ross |
| 5,513,238 A | 4/1996 | Leber et al. |
| 5,560,358 A | 10/1996 | Arnold et al. |
| 5,660,200 A | 8/1997 | Paes |
| 5,695,514 A | 12/1997 | Chin |
| 5,738,666 A | 4/1998 | Watson et al. |
| 5,755,758 A | 5/1998 | Woloszko et al. |
| 5,766,195 A | 6/1998 | Nobles |
| 5,782,741 A | 7/1998 | Bradshaw et al. |
| 5,797,878 A | 8/1998 | Bleam |
| 5,800,376 A | 9/1998 | Watson et al. |
| 5,843,013 A | 12/1998 | Lecuyer et al. |
| 5,865,748 A | 2/1999 | Co et al. |
| 5,911,685 A | 6/1999 | Siess et al. |
| 5,921,979 A | 7/1999 | Kovac et al. |
| 5,921,992 A | 7/1999 | Costales et al. |
| 5,928,182 A | 7/1999 | Kraus et al. |
| 5,935,084 A | 8/1999 | Southworth |
| 5,971,997 A | 10/1999 | Guthrie et al. |
| 5,983,141 A | 11/1999 | Sluijter et al. |
| 6,041,101 A | 3/2000 | Kooy et al. |
| 6,048,306 A | 4/2000 | Spielberg |
| 6,050,969 A | 4/2000 | Kraus |
| 6,110,155 A | 8/2000 | Baudino |
| 6,113,613 A | 9/2000 | Spaulding |
| 6,120,465 A | 9/2000 | Guthrie et al. |
| 6,122,541 A | 9/2000 | Cosman et al. |
| 6,146,380 A | 11/2000 | Racz et al. |
| 6,161,048 A | 12/2000 | Sluijter et al. |
| 6,167,295 A | 12/2000 | Cosman |
| 6,193,682 B1 | 2/2001 | Ahmed |
| 6,275,725 B1 | 8/2001 | Cosman |
| 6,348,042 B1 | 2/2002 | Warren |
| 6,371,464 B1 | 4/2002 | Porche et al. |
| 6,383,159 B1 | 5/2002 | Saul et al. |
| 6,402,771 B1 | 6/2002 | Palmer et al. |
| 6,415,823 B1 | 7/2002 | Vasek et al. |
| 6,436,142 B1 | 8/2002 | Pees et al. |
| 6,506,199 B2 | 1/2003 | Rogers et al. |
| 6,540,727 B2 | 4/2003 | Harper et al. |
| 6,540,736 B2 | 4/2003 | Harper et al. |
| 6,689,085 B1 | 2/2004 | Rubenstein et al. |
| 6,692,493 B2 | 2/2004 | McGovern et al. |
| 6,731,976 B2 | 5/2004 | Penn et al. |
| 6,852,122 B2 | 2/2005 | Rush |
| 6,871,740 B1 | 3/2005 | Cao |
| 6,881,210 B2 | 4/2005 | Wilson |
| 6,883,241 B2 | 4/2005 | Moskowitz et al. |
| 6,913,589 B2 | 7/2005 | Dextradeur et al. |
| 6,916,310 B2 | 7/2005 | Sommerich |
| 6,919,100 B2 | 7/2005 | Narayanan |
| 6,953,444 B2 | 10/2005 | Rosenberg |
| 7,025,739 B2 | 4/2006 | Saul |
| 7,036,369 B2 | 5/2006 | Keppner et al. |
| 7,037,288 B2 | 5/2006 | Rosenberg et al. |
| 7,059,330 B1 | 6/2006 | Makower et al. |
| 7,069,779 B2 | 7/2006 | Zumkehr et al. |
| 7,094,214 B2 | 8/2006 | Dextradeur et al. |
| 7,172,571 B2 | 2/2007 | Moskowitz et al. |
| 7,181,963 B2 | 2/2007 | Bork |
| 7,189,221 B2 | 3/2007 | Silverberg et al. |
| 7,192,413 B2 | 3/2007 | Kraus et al. |
| 7,195,640 B2 | 3/2007 | Falotico et al. |
| 7,226,441 B2 | 6/2007 | Kulessa |
| 7,235,060 B2 | 6/2007 | Kraus |
| 7,261,735 B2 | 8/2007 | Llanos et al. |
| D550,348 S | 9/2007 | Copley et al. |
| 7,286,879 B2 | 10/2007 | Wallace |
| 7,300,434 B2 | 11/2007 | Moskowitz et al. |
| 7,303,758 B2 | 12/2007 | Falotico et al. |
| 7,304,277 B2 | 12/2007 | Weber |
| 7,309,330 B2 | 12/2007 | Bertrand et al. |
| 7,320,676 B2 | 1/2008 | Miesel |
| 7,334,582 B2 | 2/2008 | Bertrand et al. |
| 7,334,594 B2 | 2/2008 | Ludin |
| 7,415,309 B2 | 8/2008 | McIntyre |
| 7,510,533 B2 | 3/2009 | Mauge et al. |
| 7,530,963 B2 | 5/2009 | Albright |
| 7,582,068 B2 | 9/2009 | Koullick et al. |
| 7,585,280 B2 | 9/2009 | Wilson et al. |
| 7,614,743 B2 | 11/2009 | Geiger |
| 7,620,456 B2 | 11/2009 | Gliner et al. |
| 7,695,731 B2 | 4/2010 | Falotico et al. |
| 7,715,896 B2 | 5/2010 | Ramzipoor et al. |
| 7,736,312 B2 | 6/2010 | Taylor et al. |
| 7,771,381 B2 | 8/2010 | McCusker et al. |
| 7,806,924 B2 | 10/2010 | Falotico et al. |
| 7,812,290 B2 | 10/2010 | Weber |
| 7,842,004 B2 | 11/2010 | Kassem |
| 7,846,940 B2 | 12/2010 | Falotico et al. |
| 7,875,282 B2 | 1/2011 | Falotico et al. |
| 7,922,685 B2 | 4/2011 | Rosenberg |
| 8,015,977 B2 | 9/2011 | Bertrand et al. |
| 8,088,092 B2 | 1/2012 | McCusker et al. |
| 8,192,445 B2 | 6/2012 | Parmer et al. |
| 8,216,296 B2 | 7/2012 | Wu et al. |
| 8,389,083 B2 | 3/2013 | Atanasoska et al. |
| 8,622,978 B2 | 1/2014 | Bertrand et al. |
| 2003/0004495 A1 | 1/2003 | Saul |
| 2004/0068201 A1 | 4/2004 | Saul |
| 2004/0092908 A1 | 5/2004 | Harper et al. |
| 2005/0043669 A1 | 2/2005 | Rosenberg |
| 2005/0043670 A1 | 2/2005 | Rosenberg |
| 2005/0055009 A1 | 3/2005 | Rosenberg |
| 2005/0137579 A1* | 6/2005 | Heruth ............ A61M 5/14276 604/536 |
| 2005/0256510 A1 | 11/2005 | Moskowitz et al. |
| 2006/0079927 A1 | 4/2006 | Kaemmerer et al. |
| 2006/0211944 A1 | 9/2006 | Mauge et al. |
| 2006/0211945 A1 | 9/2006 | Mauge et al. |
| 2006/0222756 A1 | 10/2006 | Lentz et al. |
| 2006/0224102 A1 | 10/2006 | Glenn |
| 2007/0004999 A1 | 1/2007 | Miethke |
| 2007/0197952 A1 | 8/2007 | Stiger |
| 2007/0203516 A1 | 8/2007 | Nayak |
| 2008/0039768 A1 | 2/2008 | Francis |
| 2008/0039770 A1 | 2/2008 | Francis et al. |
| 2008/0082036 A1 | 4/2008 | Trescony et al. |
| 2008/0140051 A1 | 6/2008 | Bei et al. |

(56) References Cited

U.S. PATENT DOCUMENTS

| | | |
|---|---|---|
| 2008/0249458 A1 | 10/2008 | Yamasaki |
| 2009/0105725 A1 | 4/2009 | O'Connor et al. |
| 2010/0249691 A1 | 9/2010 | Van Der Mooren et al. |
| 2010/0303722 A1* | 12/2010 | Jin .......................... A61L 27/30 424/9.1 |
| 2012/0232462 A1 | 9/2012 | Miethke |

* cited by examiner

OCCLUSION RESISTANT CATHETER AND METHOD OF USE

CROSS-REFERENCE TO RELATED APPLICATIONS

This application claims the benefit under 35 U.S.C. 119 of U.S. Provisional Patent Application 61/801,232 filed Mar. 15, 2013, and entitled "Occlusion Resistant Catheter and Method of Use."

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present disclosure relates to implantable occlusion resistant fluid interfaces, such as catheter tips used in the treatment of hydrocephalus.

BACKGROUND

One application of the occlusion resistant catheters disclosed herein is in shunting systems for cerebral-spinal fluid for use in treating hydrocephalus. Conventional shunting systems used for this purpose typically include three components: a ventricular catheter portion; a peritoneal catheter portion; and a valve located between the two catheter portions. The catheter portions typically are formed from a flexible synthetic polymer such as silicone rubber. A proximal end of the ventricular catheter portion is configured for insertion in a cerebral ventricle. A distal end of the peritoneal catheter portion is configured for insertion in a body cavity, or in some cases configured to drain fluid outside of the body. In many cases it would be preferable that all three components be implanted subcutaneously and left in place for many years.

The purpose of the shunting systems when treating hydrocephalus is to affect periodic drainage of excess cerebral-spinal fluid from the cerebral ventricle. The cerebral ventricle that is typically drained is ventricle III. The cerebral-spinal fluid is drained from the cerebral ventricle in order to maintain proper endro-cranial tension or pressure at normal physiological values.

Conventional shunting systems for treating hydrocephalus suffer from occlusion of the fluid path through the shunt, typically at the inlet in the proximal end of the ventricular catheter portion and/or at the outlet in the distal end of the peritoneal catheter portion. Many attempts have been made to design clog resistant tips and orifices, however most have not met with much success. Blockage in the fluid path typically occurs as a result of tissue ingrowth and/or protein buildup in and around these orifices, often the result of the deposition of filaments of fibrin. Such blockage will often render the shunting systems useless in less than two years after implantation, requiring frequent replacement of the shunt. Such replacement procedures can be expensive, uncomfortable for the patient, and expose the patient to unnecessary complications associated with the procedures.

Further information relating to the treatment of hydrocephalus with conventional shunting systems may be found in U.S. Pat. No. 4,375,816 to Labianca and U.S. Pat. No. 7,582,068 to Koullick et al.

What is needed and is not provided by the prior art are implantable shunting systems that can be used in the treatment of hydrocephalus, and in other medical applications such as hemodialysis, without occlusion and tissue ingrowth.

SUMMARY OF THE DISCLOSURE

According to some aspects of the present disclosure, an implantable occlusion resistant fluid interface may be configured to prevent inflammatory cells from binding to its surface(s), as the inflammatory process and associated tissue can greatly reduce the necessary fluid flow of the implantable. In some embodiments, the occlusion resistant interface is provided with a housing, an orifice and a catheter port. The housing is formed from at least one biocompatible material and may be configured without sharp edges or corners. The housing may at least partially define an internal housing cavity. The orifice member is formed from at least one biocompatible material and may at least partially define an orifice between the internal housing cavity and an exterior of the housing. In some embodiments, the orifice has an elongated transverse cross-section configured with a length that is at least four times its maximum width. The catheter port is located on the housing and is configured to couple with a catheter such that the internal housing cavity is in fluid communication with a lumen of the catheter when the catheter is coupled to the catheter port.

In some embodiments, the maximum width of the transverse cross-section of the orifice does not exceed 0.003 inches. The orifice member may be configured to be movable with respect to the housing. In some embodiments, the movable orifice member includes a plate. The housing may be formed from at least two separate pieces that are joined together to captivate the plate therebetween. In some embodiments, each of the at least two separate pieces is an elongated hemispherical toroidal shell that form a completed elongated toroidal shell when joined together. The plate is located across a central aperture of the toroid in these embodiments.

According to other aspects of the present disclosure, an implantable occlusion resistant shunt is provided with a fluid interface as described above. The shunt is also provided with a flexible catheter formed from a biocompatible material. The catheter has a first end and a second end, with the first end coupled with the catheter port of the fluid interface. In some embodiments, the shunt further comprises a second fluid interface as described above. In these embodiments, the second end of the catheter is coupled with the catheter port of the second fluid interface.

According to other aspects of the present disclosure, a method of treating hydrocephalus is disclosed. In some embodiments, the method comprises providing a shunt as described above, and implanting the fluid interface and the first end of the shunt catheter within a patient adjacent to brain tissue. The method may also include implanting a remainder of the catheter within the patient, and locating the second end of the catheter in a region of the patient away from the brain tissue.

In some embodiments, an implantable occlusion resistant fluid interface comprises a housing, an orifice member and a catheter port. In these embodiments, the housing is formed from at least one biocompatible material and is configured without sharp edges or corners. The housing at least partially defines an internal housing cavity. The orifice member is also formed from at least one biocompatible material and it at least partially defines an orifice between the internal housing cavity and an exterior of the housing. The orifice has an elongated transverse cross-section configured with a maximum width and configured with a length that is at least four times the maximum width. The catheter port is located on the housing and is configured to couple with a catheter such that the internal housing cavity is in fluid communication with a lumen of the catheter when coupled to the catheter port.

In some embodiments of the above fluid interface, the maximum width of the transverse cross-section of the orifice does not exceed 0.003 inches. The orifice member may be movable with respect to the housing and may comprise a plate. The housing may be formed from at least two separate pieces that are joined together to captivate the plate therebetween. The at least two separate pieces may each be an elongated hemispherical toroidal shell that form a completed elongated toroidal shell when joined together, and the plate may be located across a central aperture of the toroid. In some embodiments, the orifice member comprises nano-ripples formed by ion blasting on one or more surfaces. The nano-ripples may have a height of about 50 nm or less and a spacing of about 52 nm or less.

In some embodiments, an implantable occlusion resistant shunt comprises a fluid interface as described above, and a flexible catheter formed from a biocompatible material. In these embodiments, the flexible catheter has a first end and a second end, and the first end is coupled with the catheter port of the fluid interface. The shunt may further comprise a second fluid interface as described above, wherein the second end of the catheter is coupled with the catheter port of the second fluid interface.

In some embodiments, a method of treating hydrocephalus comprises providing a shunt as described above and implanting the fluid interface and the first end of the catheter within a patient adjacent to brain tissue. These methods further comprise implanting a remainder of the catheter within the patient and locating the second end of the catheter in a region of the patient away from the brain tissue.

In some embodiments, an implantable occlusion resistant fluid interface comprises a housing, an agitator and a catheter. In these embodiments, the housing is formed from at least one biocompatible material and configured without sharp edges or corners. The housing at least partially defines an internal housing cavity. The agitator is formed from at least one biocompatible material and at least partially defines an orifice between the internal housing cavity and an exterior of the housing. The agitator is configured to passively move longitudinally between a first position and a second position, thereby changing fluid flow patterns within the internal housing cavity. The catheter port is located on the housing and is configured to couple with a catheter such that the internal housing cavity is in fluid communication with a lumen of the catheter when coupled to the catheter port.

In some embodiments of the above fluid interface, the agitator is cylindrically shaped. The housing may comprise a transverse cross-section that is generally triangular in shape. The transverse cross-section may comprise three rounded apexes and three inwardly curving side faces spanning between the three apexes. Each of the three apexes may comprise a longitudinally extending internal channel that overlaps with and is in fluid communication with the internal housing cavity. Each of the three side faces may comprise an elongated slot in fluid communication with the internal housing cavity and with the exterior of the housing.

In some embodiments, an implantable occlusion resistant fluid interface comprises a housing, a rotor and a catheter port. In these embodiments, the housing is formed from at least one biocompatible material and is configured without sharp edges or corners. The housing at least partially defines an internal housing cavity. The rotor is formed from at least one biocompatible material and is rotatably mounted within the internal housing cavity such that a fluid flow in the cavity will cause the rotor to passively rotate. The catheter port is located on the housing and is configured to couple with a catheter such that the internal housing cavity is in fluid communication with a lumen of the catheter when coupled to the catheter port.

In some embodiments of the above fluid interface, the rotor comprises a plurality of turbine blades. The rotor may be elongated and have two ends, and the fluid interface may further comprise a ball bearing located at each of the two rotor ends configured to allow the rotor to passively rotate relative to the housing. The ball bearings may be made of sapphire. The housing may comprise an end cap having at least one vent hole therethrough. The vent hole may be configured to allow fluid to flow from the internal housing cavity, past the turbine blades and out through the vent hole to an exterior of the housing.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
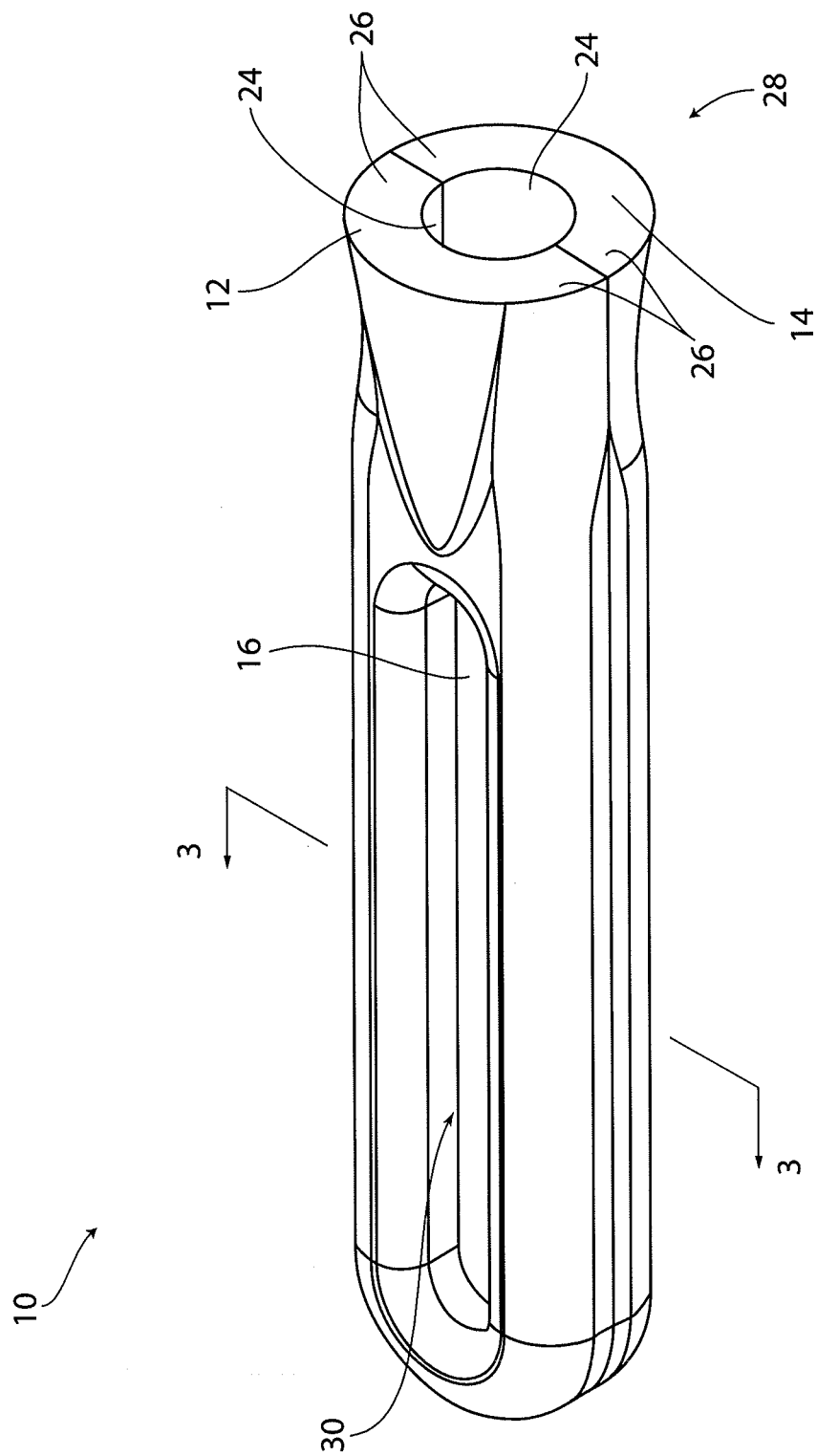
FIG. 1 is a side perspective view showing a first exemplary embodiment of an implantable fluid interface.
Figure 2:
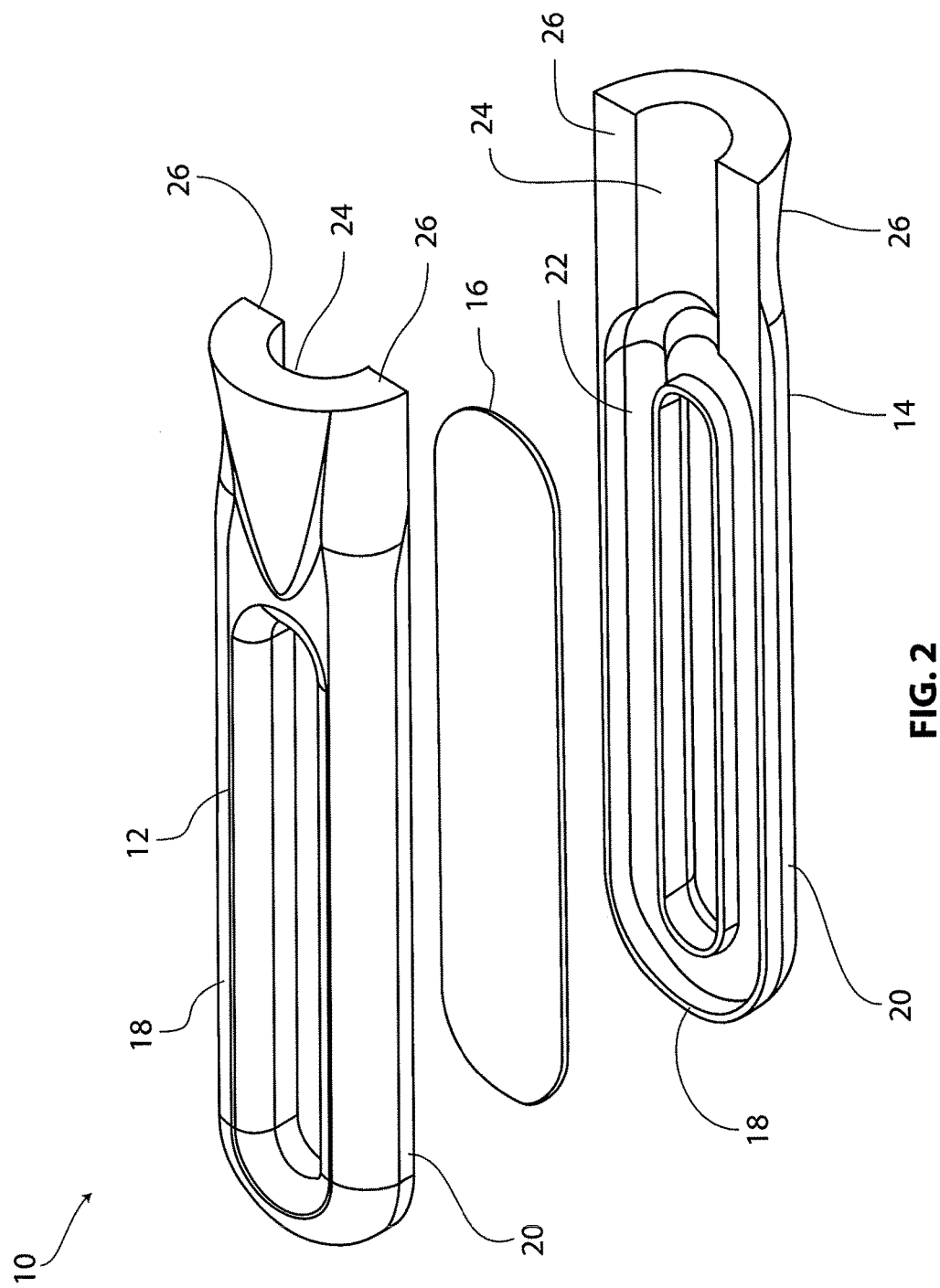
FIG. 2 is an exploded perspective view showing the components of the fluid interface of FIG. 1.
Figure 3:
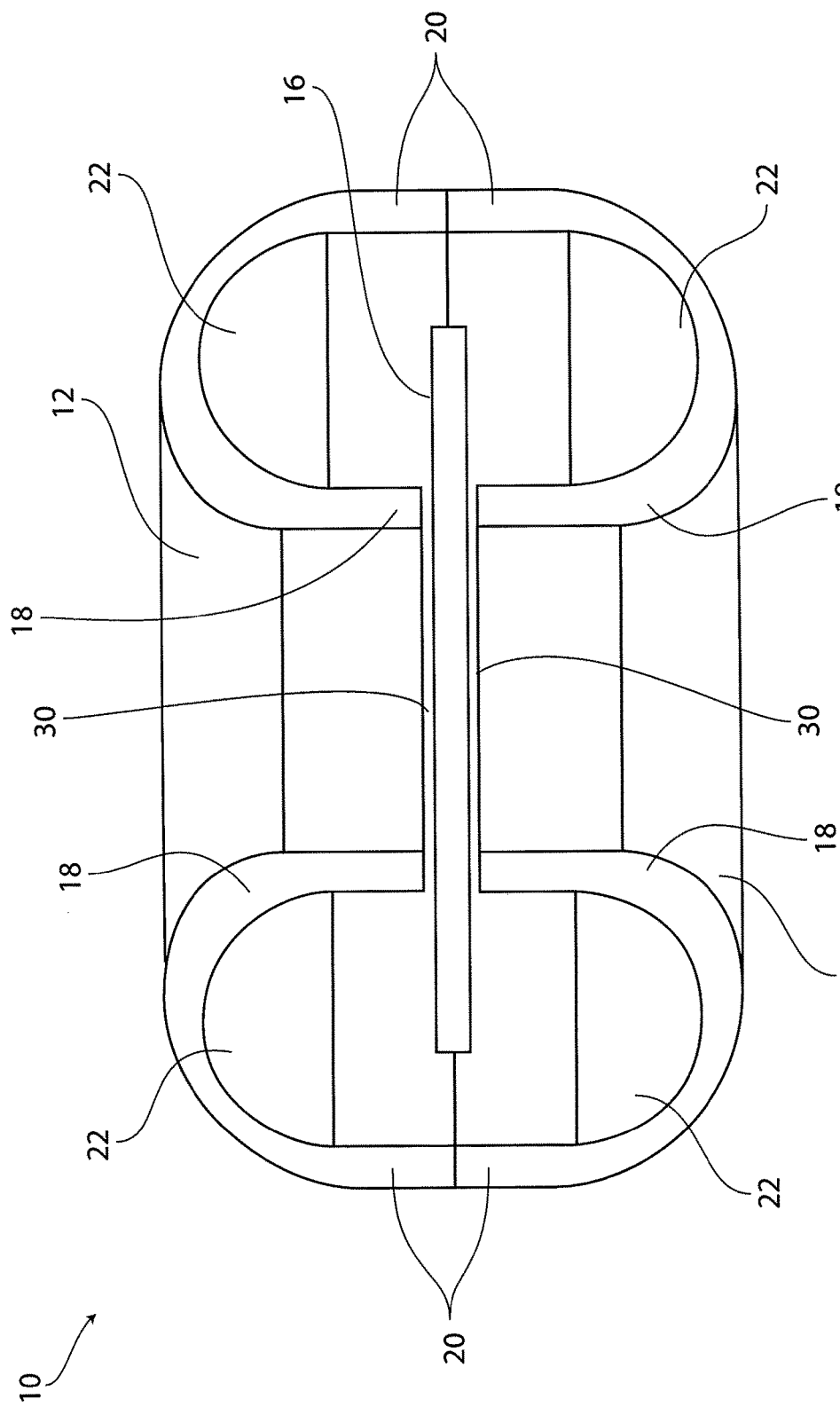
FIG. 3 is a cross-sectional view taken along Line 3-3 of FIG. 1.

Referring to FIGS. 1-3, a first exemplary embodiment of an implantable occlusion resistant fluid interface 10 is shown. In this embodiment, fluid interface 10 includes three components: a top housing shell 12, a bottom housing shell 14, and a movable orifice member plate 16. In its assembled configuration, as shown in FIG. 1, plate 16 is sandwiched between top shell 12 and bottom shell 14, and is movably captivated therebetween. In this embodiment, top shell 12 and bottom shell 14 are manufactured to be identical pieces differing only in name.

Referring to FIG. 2, the main portion of bottom shell 14 is provided with an oval shaped inner wall 18, a U-shaped outer wall 20, and a recessed portion 22 located therebetween. The right side of bottom shell 14 is provided with a trough 24 that communicates with recessed portion 22. Thickened wall sections 26 are provided on either side of trough 24. Top shell 12 includes the same features as bottom shell 14. During the assembly of device 10, the outer wall 20 of bottom shell 14 is joined with outer wall 20 of top shell 12, and the thickened wall sections 26 of bottom shell 14 are joined with the thickened wall sections 26 of top shell 12. The joining process may include laser welding, ultrasonic welding, adhesive, or other suitable joining processes. Once top shell 12 is joined with bottom shelf 14, a catheter port 28 is formed at one end of device 10 by troughs 24, as shown in FIG. 1.

Referring to FIG. 3, a cross-section of device 10 taken along line 3-3 of FIG. 1 is shown. Once the top housing shell 12 and bottom housing shell 14 are joined together as previously described, their respective recessed portions 22 together form an internal housing cavity defined by the toroidal housing of assembled device 10. As can be seen in FIG. 3, the inner walls 18 of top shell 12 and bottom shell 14 do not extend as far towards the opposing shell as do outer walls 20. This arrangement leaves room for plate 16 to be movably received between top shell 12 and bottom shell 14 with additional space remaining above and/or below plate 16 between it and inner walls 18 of top shell 12 and bottom shell 14. This additional space not only allows plate 16 to move relative to the housing of device 10, but provides at least one oval shaped orifice 30 (also shown in FIG. 1) between the internal housing cavity and the exterior of the housing (in the center portion of the toroidal housing). It can be seen from FIG. 3 that plate 16 is sized such that when it moves laterally in either direction to contact the inside of outer walls 20, the opposite side of plate 16 still remains within the space between inner walls 18. This is also true when plate 16 moves in either direction longitudinally relative to top shell 12 and bottom shell 14.

Figure 4:
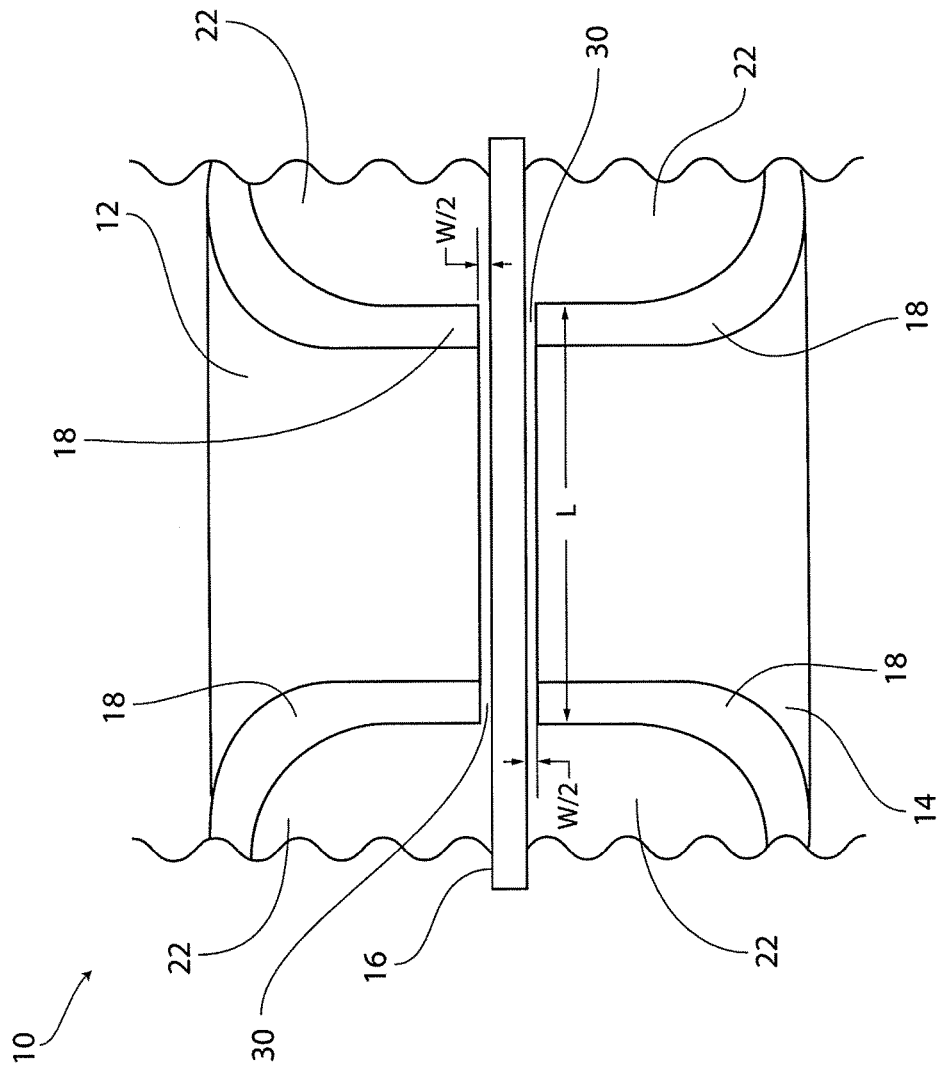
FIG. 4 is an enlarged cross-sectional view showing a portion of FIG. 3.

Referring to FIG. 4, an enlarged portion of the cross-sectional view of FIG. 3 showing plate 16 is provided. In this exemplary embodiment, plate 16 is captivated between inner walls 18 of top housing shell 12 and bottom housing shell 14, and is allowed to float therebetween, as shown in FIGS. 3 and 4. As depicted in these figures, orifice 30 can exist above and/or below plate 30. It can be appreciated that a maximum orifice width W can be defined as the distance between the upper inner walls 18 and lower inner walls 18 minus the thickness of plate 16. This maximum orifice width W would occur on the opposite side of plate 16 when it rests against either the upper inner walls 18 or the lower inner walls 18. In FIG. 4, plate 16 is depicted as being in a central position with an orifice width W/2 above the plate and another orifice having width W/2 below the plate. Orifice or orifices 30 can also be defined as having a length of at least L, as shown in FIG. 4. The length L of orifice 30 can alternatively be defined in the longitudinal direction of device 10, or even as the length of the inside circumference of inner wall 18 of either the top housing shell 12 or bottom housing shell 14.

In some embodiments, the maximum orifice width is maintained at about 0.010 inches or less. In some embodiments, the maximum orifice width is maintained at about 0.003 inches or less. In other embodiments, a mixture of orifice sizes is used. Initial testing suggests that by keeping the maximum orifice width W to these small dimensions, tissue ingrowth and/or protein buildup that would otherwise clog orifice 30 can be impeded or eliminated. To increase the flow rate through orifice 30, it is desirable for the orifice to have a larger cross-section. The orifice cross-section is defined as being transverse to the fluid flow through the orifice. This can be accomplished by maintaining the orifice width W at 0.010 inches, 0.003 inches or less and increasing the length L to create an elongated orifice. In some embodiments of the inventiveness fluid interface, the orifice has an elongated transverse cross-section configured with a length that is at least four times the maximum width. In some embodiments, the orifice length is at least 10 times the maximum width. In some embodiments the orifice length is at least 100 times the maximum width. In the exemplary embodiment shown, the device is about 0.5 inches long, has an orifice length L of about 0.7 inches (taken along the inside circumference of inner walls 18) and a maximum width W of 0.003 inches. This yields an orifice 30 having an elongated transverse cross-section configured with a length L that is more than 200 times the maximum width W.

In addition to the elongated transverse cross-section of orifice 30, the movement of plate 16 relative to orifice or orifices 30 that it partially defines contributes to impeding or eliminating tissue ingrowth and/or protein buildup that would otherwise clog the orifice(s). In some cases when device 10 is implanted within a patient, plate 16 is continuously or at least periodically moving relative to inner walls 18. Such movement can cause the orifice to be self-cleaning. The movement can also create a varying orifice size, and therefore create variable regional fluid flow near the orifice. It is believed that such variable regional fluid flow, or flow instability, contributes to impeding or eliminating tissue and/or protein buildup in and around the orifice. Conversely, it is believed that a constant, non-varying fluid flow contributes to tissue and/or protein buildup.

In some embodiments, top housing shell 12, bottom housing shell 14 and orifice member plate 16 are formed from titanium. The outside of device 10 can be ultra-electropolished. To further inhibit orifice clogging, plate 16 can be nano-etched (roughened) to help prevent tissue and proteins from forming on plate 16. This can be accomplished with ion blasting, such as with a xenon ion gun, to form nano channels or ripples on plate 16. There will be less adsorbed proteins on the modified surfaces due to a decrease of the surface energy caused by the surface modification. In some embodiments, the nano-ripples are less than about 50 nm high. In some embodiments, the nano-ripples are about 10 nm high. Initial testing indicates that if the nano-ripples are created with a spacing of about 52 nm or less, adhesion of tissue and protein to plate 16 can be prevented. Some embodiments include varied nano sized surface curvatures. These surface treatments can be applied to other surfaces of device 10 and to surfaces of other devices disclosed herein.

In some embodiments, surface treatment(s) of plate 16 are purely mechanical, as described above, without any chemical treatments or changes to the stoichiometry of the device surfaces. Advantages of purely mechanical treatments include avoidance of degradation of the material of plate 16, and also the avoidance of additional regulatory issues, such as with the U.S. Food and Drug Administration (FDA).

Figure 5:
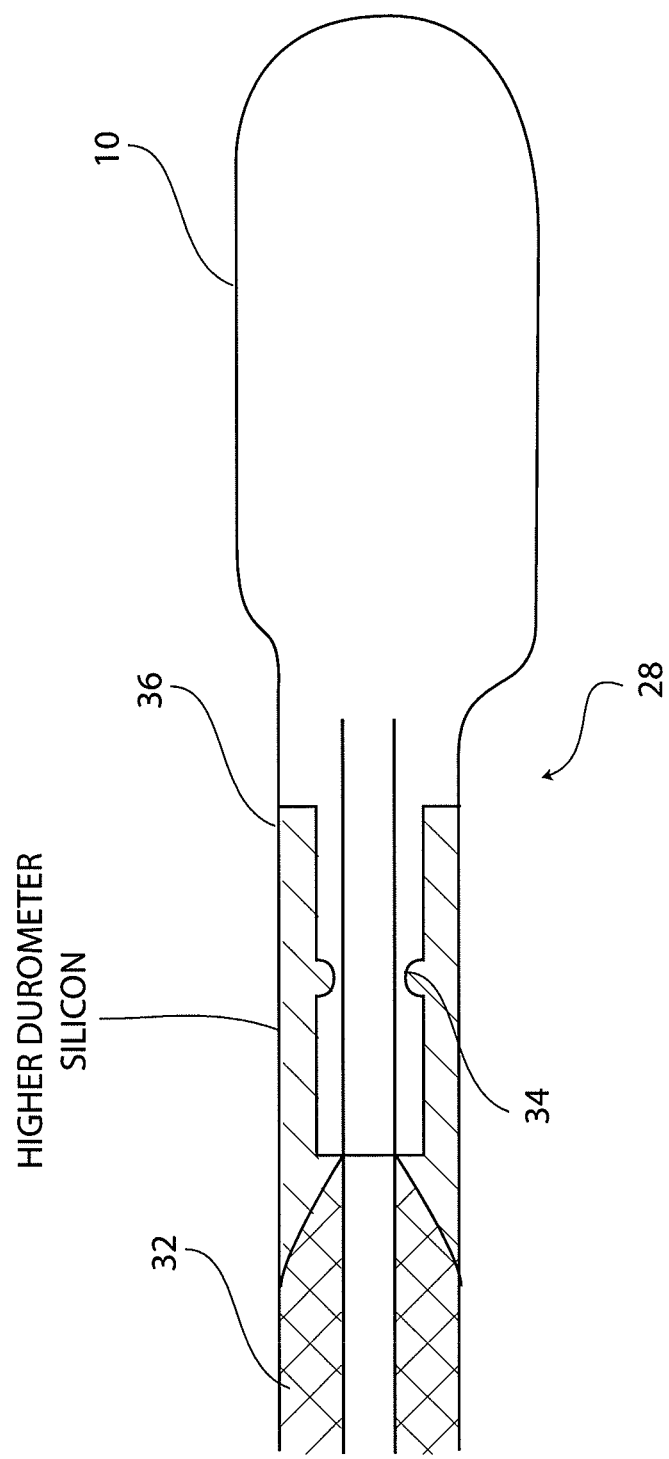
FIG. 5 is a top plan view showing an exemplary fluid interface coupled with a catheter.

As shown in FIG. 5, device 10 can be attached to one end of a catheter 32. In one embodiment, this is accomplished by welding a titanium mesh onto the neck or catheter port 28 of device 10, and then over molding the mesh with silicone to bond to catheter 32. Alternatively, a solid neck having one or more grooves 34, barbs or other recessed features may be used as the core in an over molding process. A silicon material having a higher durometer than the rest of the catheter 32 may be overmolded in the region of catheter port 28 as depicted in FIG. 5. An essentially seamless transition 36 between the catheter 32 and catheter port 28 can be created by matching the outer diameter of catheter port 28 with the outer diameter of catheter 32. This inhibits tissue ingrowth after implantation and also enables device 10 to be removed from a patient without tissue damage.

A fluid interface device 10 constructed according to aspects of the present disclosure can be located at the inlet end of a catheter, at the outlet end, or both, when the catheter is used to move fluid from one region of a patient to another.

The exterior surfaces of device 10 can be roughened to reduce surface tension. This in turn can alleviate air bubbles from adhering to device 10 during insertion of the device into the patient, which would otherwise cause adverse effects.

In an alternative embodiment (not shown), the principles of the present disclosure can be used to construct a device having a movable ball instead of a movable plate. In such an embodiment, the ball can partially define one or more orifices, such as round holes located on opposite sides of a housing.

Figure 6:
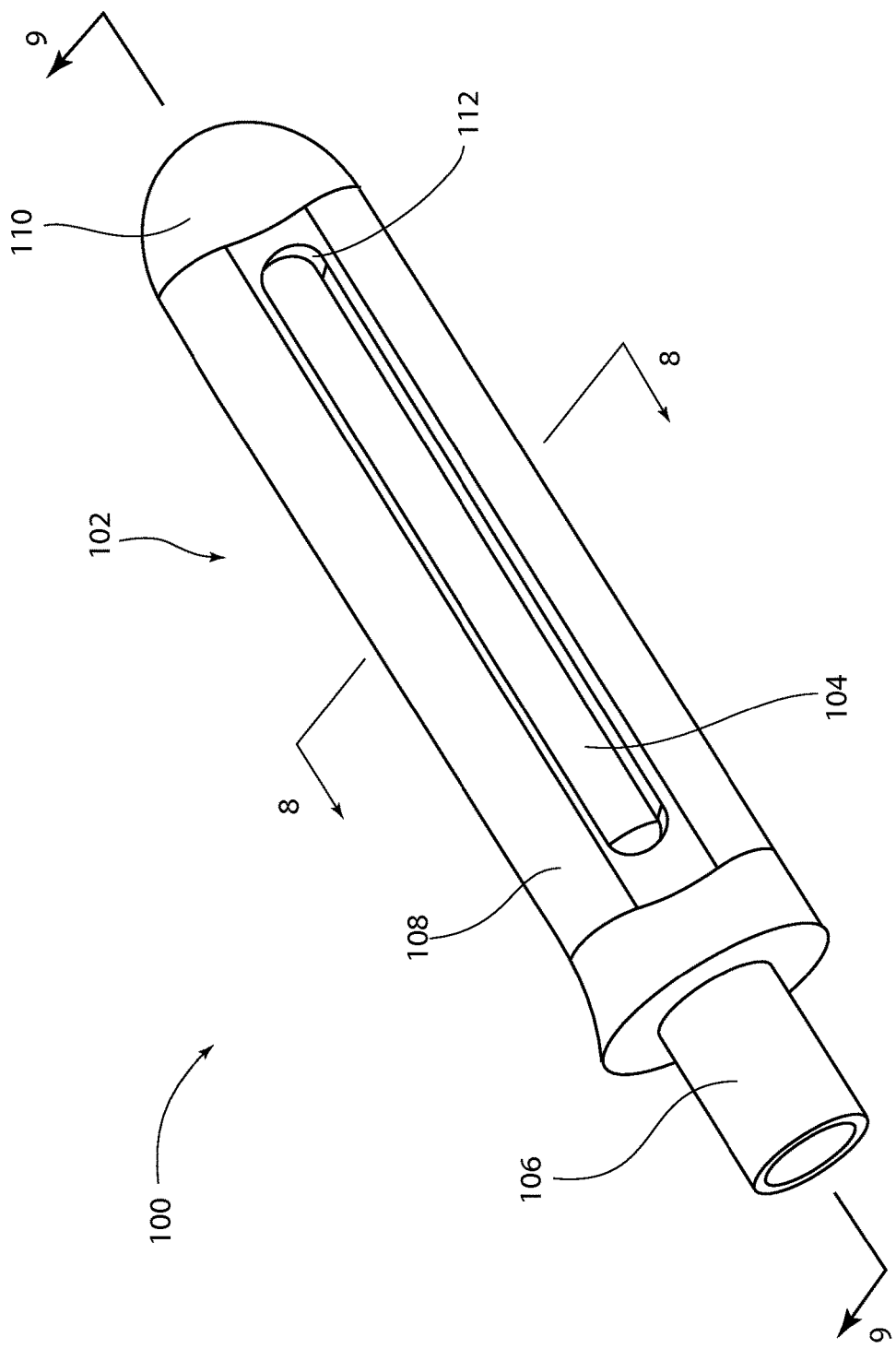
FIG. 6 is a perspective view showing a second exemplary embodiment of an implantable fluid interface.
Figure 7:
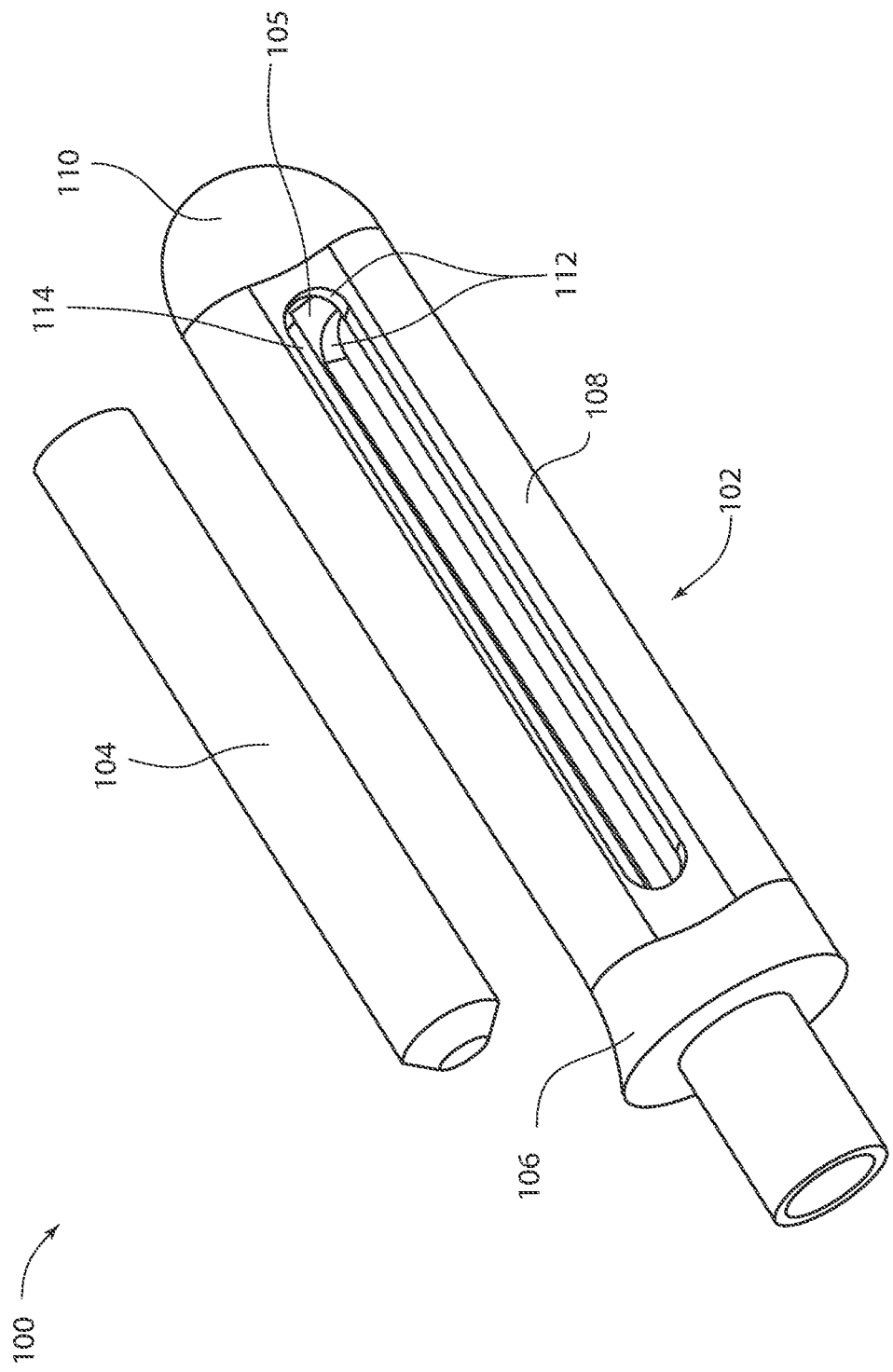
FIG. 7 is an exploded perspective view showing the components of the fluid interface of FIG. 6.

Referring to FIGS. 6-9, a second exemplary embodiment of an implantable occlusion resistant fluid interface 100 is shown. In this embodiment, fluid interface 100 includes an elongated housing 102 and a cylindrical agitator 104 captivated within a central void 105 inside housing 102. As best seen in FIGS. 6 and 7, housing 102 comprises a proximal portion 106, a middle portion 108, and a distal portion 110. Housing portions 106, 108 and 110 may be separate components that are joined together during assembly, or one or more of the components may be integrally formed. Proximal housing portion 106 comprises a fitting configured to couple to a catheter. A central lumen through proximal portion 106 is in fluid communication with central void 105 inside middle portion 108. Middle portion 108 is provided with three elongated slot 112 that provide fluid communication between central void 105 inside middle portion 108 and the exterior of device 100.

Figure 8:
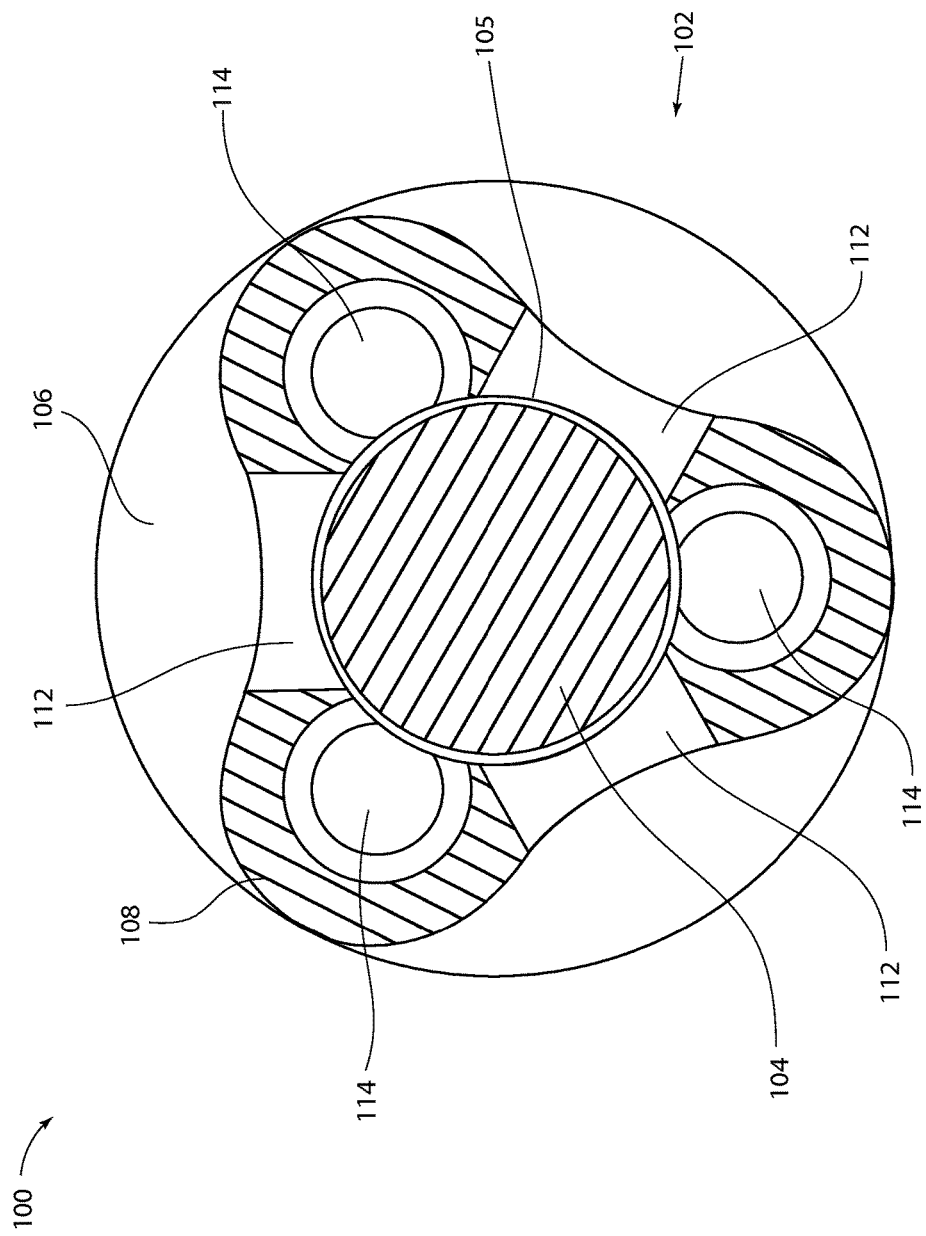
FIG. 8 is a cross-sectional view taken along Line 8-8 of FIG. 6.

Referring to FIG. 8, middle housing portion 108 as a transverse cross-section that is generally triangular in shape, but has rounded apexes and inwardly curving side faces. Each apex or lobe is provided with a longitudinally extending channel 114 that overlaps with and is in fluid communication with central void 105. In some embodiments, agitator 104 has a diameter of 0.059 inches and central void 105 has a diameter of 0.062 inches, leaving an even gap of about 0.0015 inches between agitator 104 and central void 105 on all sides, or a maximum gap of about 0.003 inches on one side. In some embodiments, channels 114 have a diameter of 0.032 inches.

Figure 9:
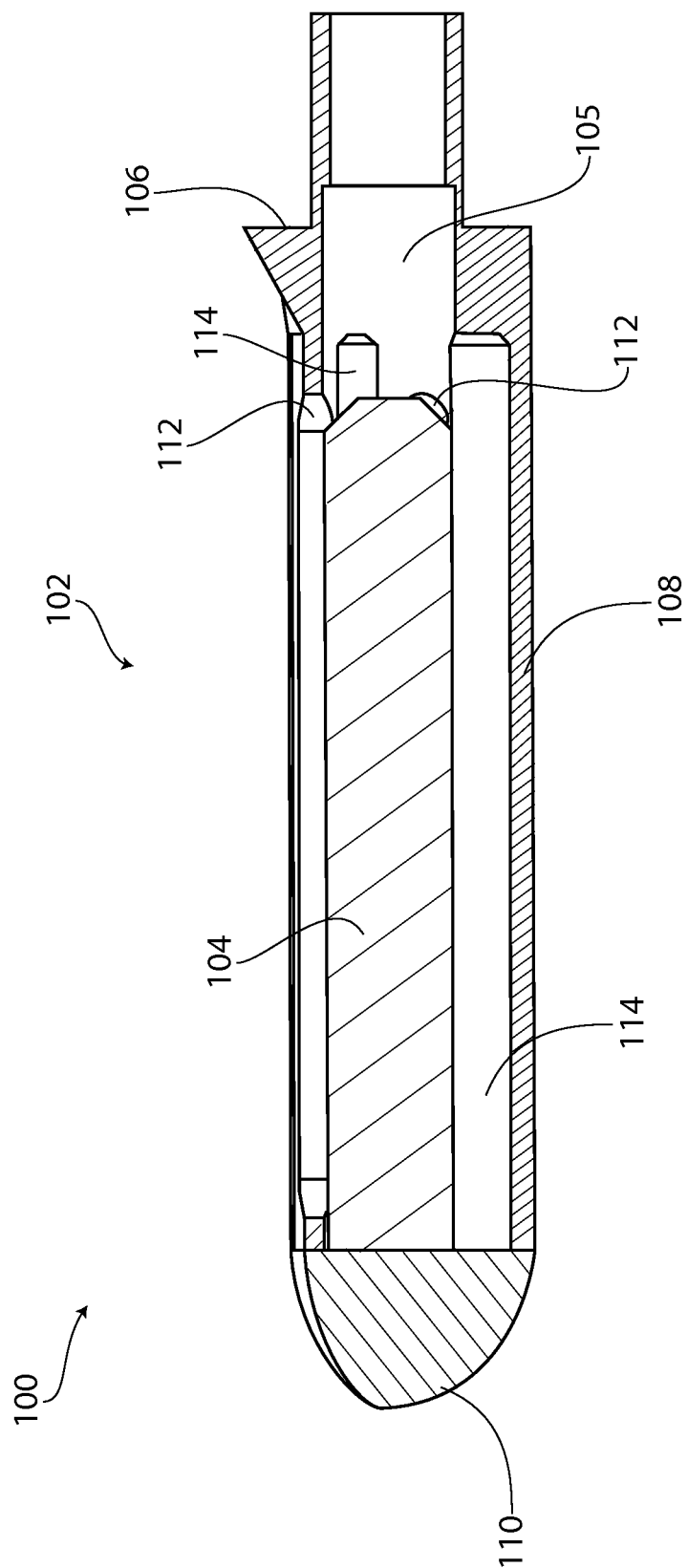
FIG. 9 is a cross-sectional view taken along Line 9-9 of FIG. 6.
Figure 10:
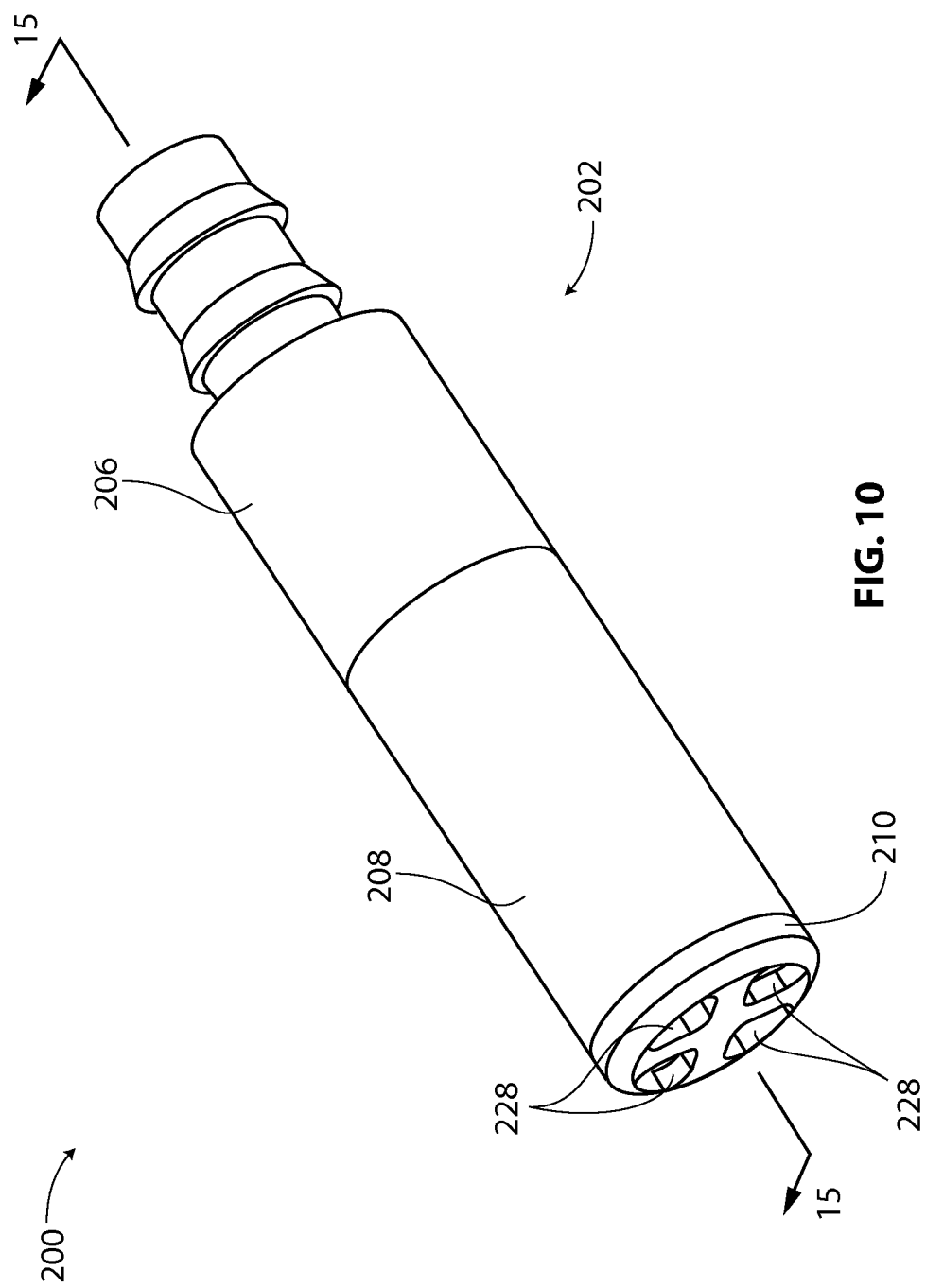
FIG. 10 is a perspective view showing a third exemplary embodiment of an implantable fluid interface.

As best seen in FIGS. 6 and 9, distal housing portion 110 is generally hemispherical in shape and is contoured to mate smoothly with the apexes and inwardly curving side faces of middle housing portion 108. Similarly, proximal housing portion 106 has a larger cylindrical portion that is also contoured to mate smoothly with the apexes and inwardly curving side faces of middle housing portion 108. The outer diameter of the larger cylindrical portion of proximal housing portion 106 may be identical to the outer diameter of the catheter it mates with. With the above described contours and dimensions, device 100 may be more easily implanted and/or removed, and may reside within a patient without causing trauma to adjacent tissue.

Referring to FIG. 9, a longitudinal cross-section of device 100 is shown. As can be seen, the length of agitator 104 is shorter than the length of central void 105 so that agitator 104 may slide longitudinally within central void 105. With this arrangement, agitator 104 may passively move within central void 105 when the orientation of device 100 changes and or the direction of fluid flow through central void 105 changes. For example, when the distal end 110 of device 100 is lowered and or fluid is flowing in a distal direction, agitator 104 may move distally. Conversely, when the distal end 110 of device 100 is raised and or fluid is flowing in a proximal direction, agitator 104 may move proximally. Such changes in fluid direction may be caused by the use of a fluid bulb in fluid communication with the catheter (not shown) to back flush the catheter system. Longitudinal movement of agitator 104 may serve to disrupt any tissue ingrowth and or protein build up that may be starting to occur within device 100, and or may serve to change the fluid flow paths when the fluid flow changes direction, thereby inhibiting tissue ingrowth and or protein build up.

In the exemplary embodiment shown in FIGS. 6-9, device 100 has an overall length of about 0.65 inches and has a maximum diameter of about 0.135 inches.

Figure 11:
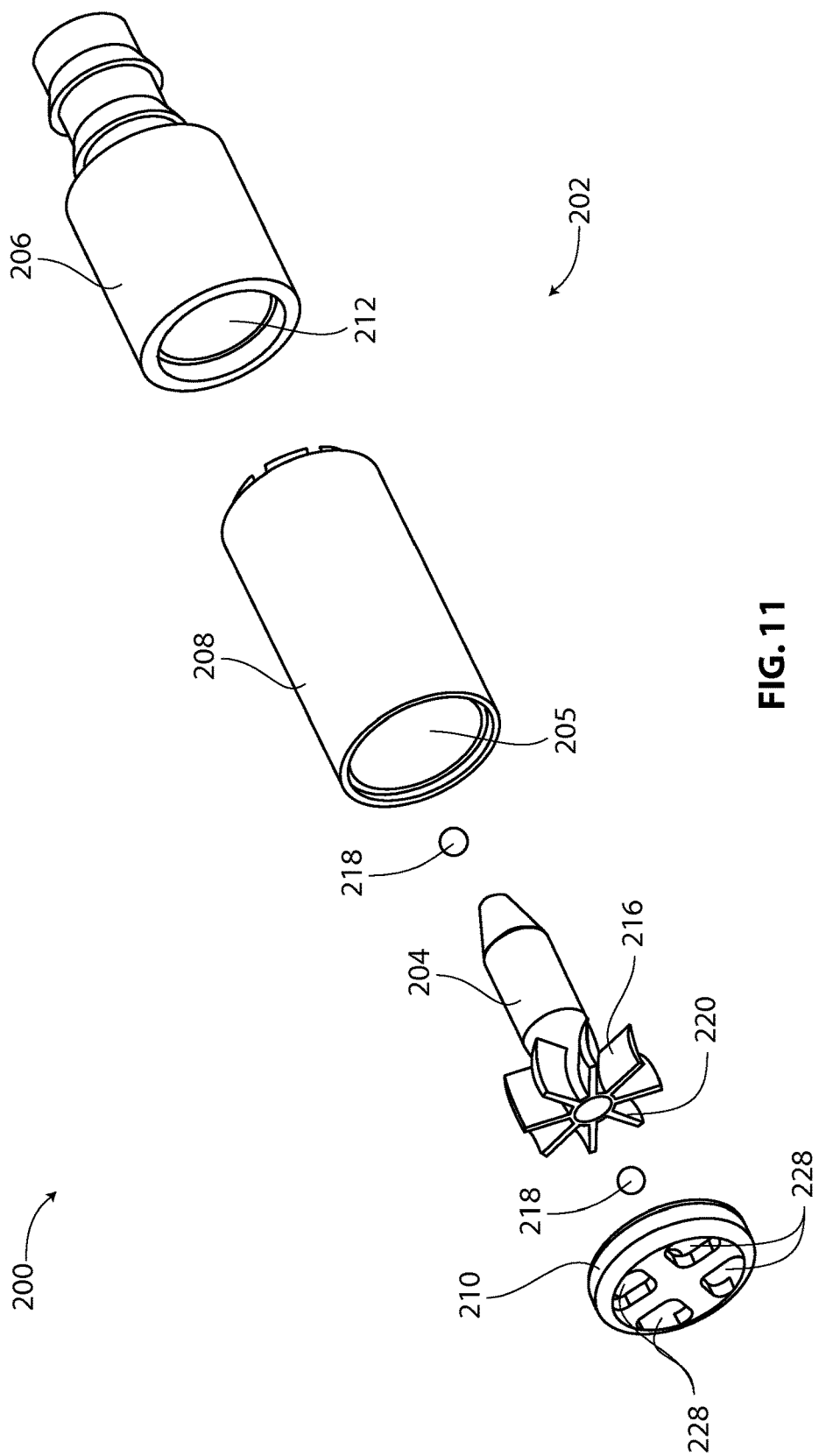
FIG. 11 is an exploded perspective view showing the components of the fluid interface of FIG. 10.
Figure 12:
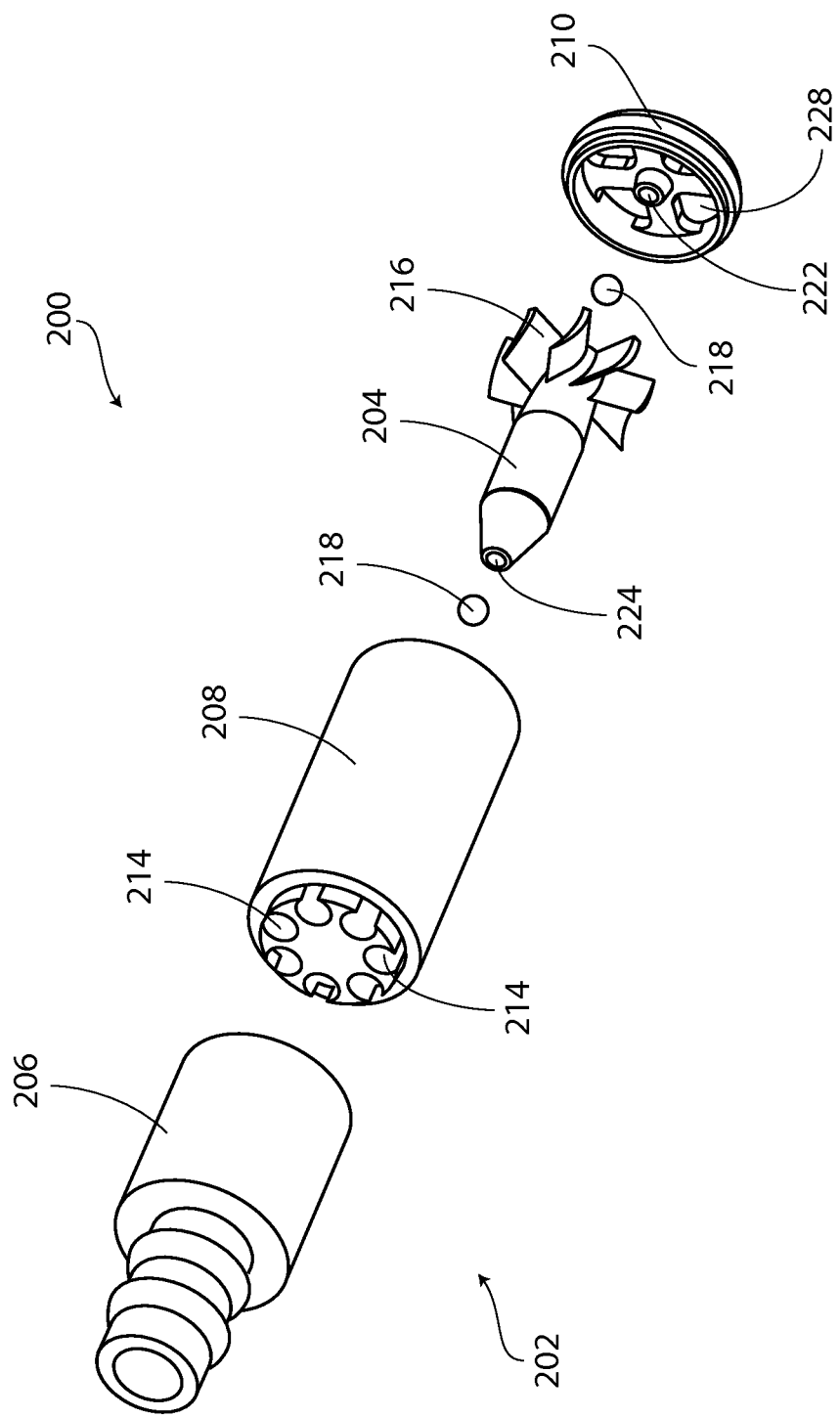
FIG. 12 is another exploded perspective view taken from an opposite direction from that of FIG. 11.
Figure 13:
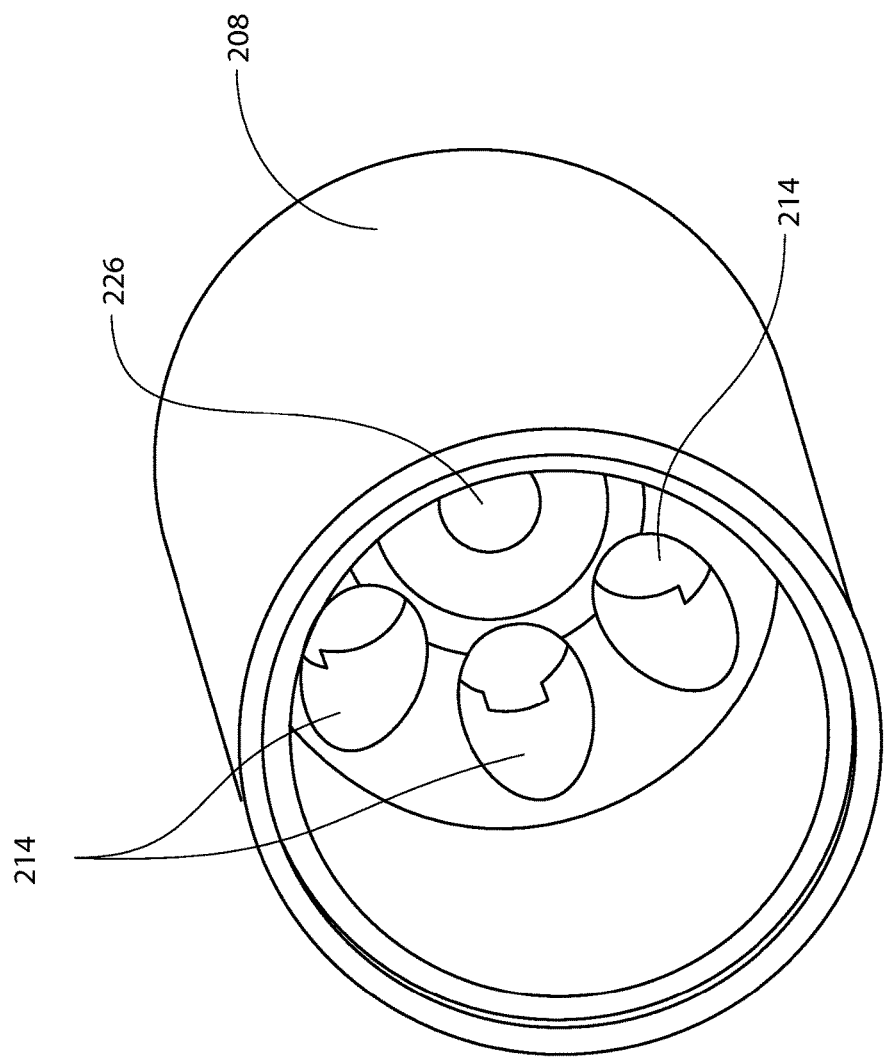
FIG. 13 is an enlarged perspective view of the middle housing portion of the fluid interface of FIG. 10.

Referring to FIGS. 10-15, a third exemplary embodiment of an implantable occlusion resistant fluid interface 200 is shown. In this embodiment, fluid interface 200 includes a housing 202 and a rotor 204 (shown in FIG. 11) rotatably disposed within a central cavity 205 inside housing 202. As best seen in FIGS. 11 and 12, housing 202 comprises a proximal portion 206, a middle portion 208, and a distal end cap 210. Housing portions 206, 208 and 210 may be separate components that are joined together during assembly, or one or more of the components may be integrally formed. Proximal housing portion 206 comprises a double-barbed fitting configured to couple to a catheter. A central lumen 212 through proximal portion 206 is in fluid communication through apertures 214 with central void 205 inside middle portion 208.

Referring to FIG. 11, rotor 204 comprises a series of radially extending turbine blades 216 disposed around its distal end. Rotor 204 is received within central cavity 205 inside middle housing portion 208 and captivated therein when distal cap 210 is attached to the distal end of middle housing portion 208 during assembly. Rotor 204 is allowed to freely rotate about a longitudinal axis by virtue of its being mounted between two ball bearings 218, which in some embodiments are made of sapphire. The distal most ball 218 is located between a circular recess 220 in the distal end of rotor 204 and a circular recess 222 on the proximal side of distal end cap 210 (shown in FIG. 12.) The proximal most ball 218 is located between a circular recess 224 on the proximal end of rotor 204 (shown in FIG. 12) and a circular recess 226 located within middle housing portion 208 (shown in FIGS. 13 and 14.) The vent holes 228 are provided through distal end cap 210 to allow fluid to flow from central cavity 205 past turbine blades 216 and out through vent holes 228 to the exterior of device 200, and or along the same path in the opposite direction. The flow of fluid past turbine blades 216 causes rotor 204 to rotate about its longitudinal axis. The distal most edges of turbine blades 216 may be located very close to vent holes 228 (such as within about 0.005 inches or less) such that the movement of turbine blades 216 disrupts tissue, protein and other matter from adhering to end cap 210.

Figure 14:
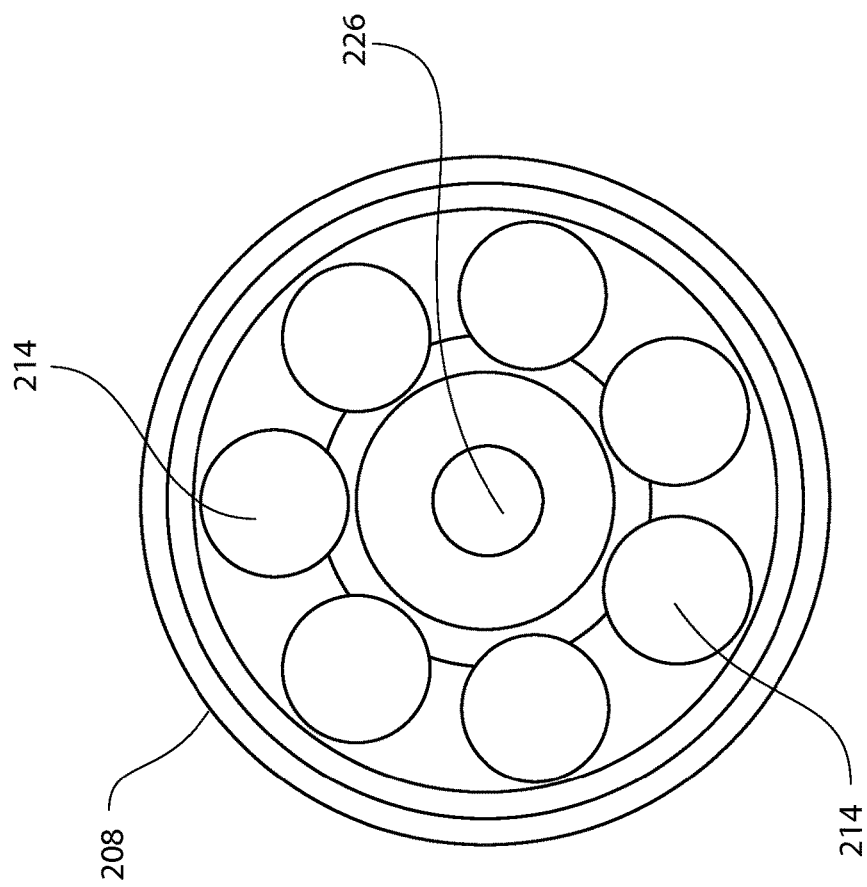
FIG. 14 is a proximally-looking end elevation view of the middle housing portion of the fluid interface of FIG. 10.
Figure 15:
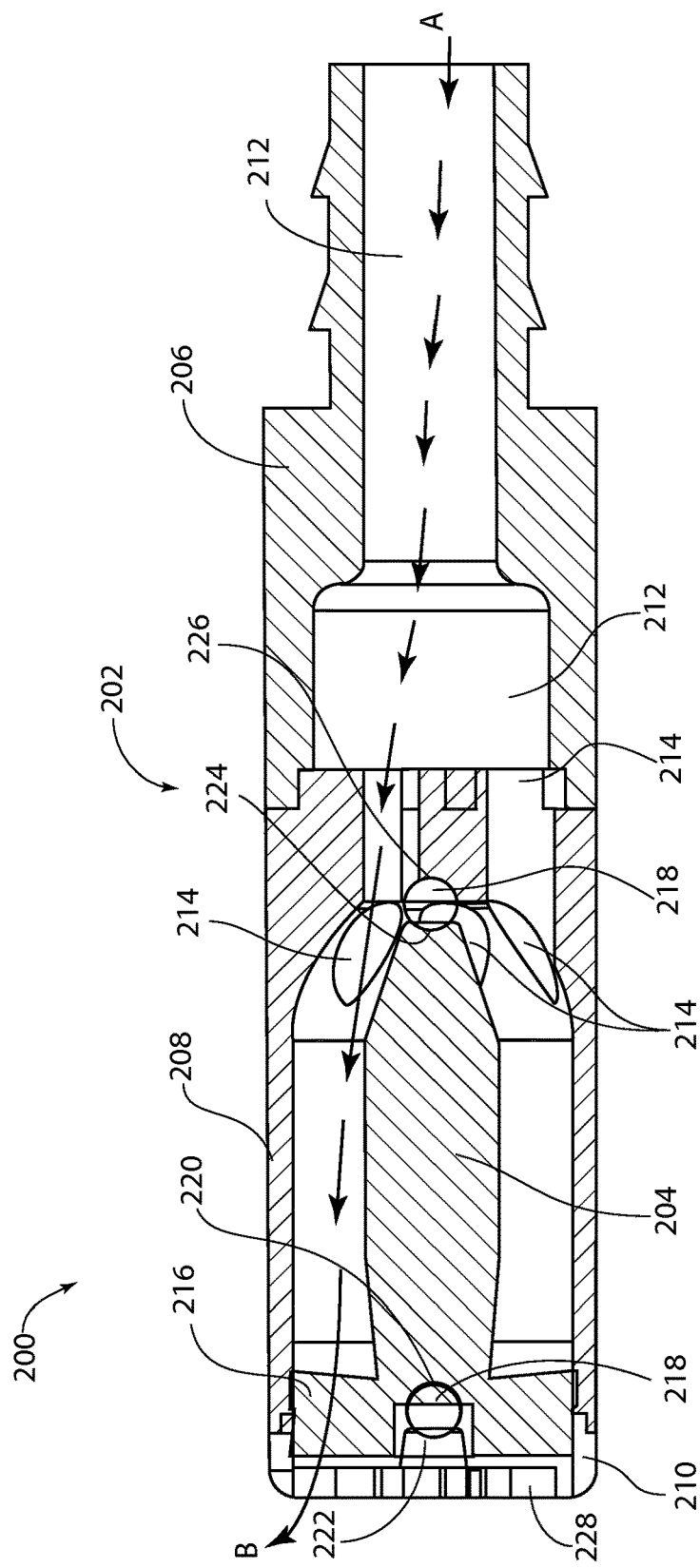
FIG. 15 is a cross-sectional view taken along Line 15-15 of FIG. 10.

Referring to FIG. 14, a longitudinal cross-section of device 200 is shown. Representative fluid flow is depicted with arrows between point A and point B. Fluid flow may also be in the opposite direction.

In the exemplary embodiment shown in FIGS. 10-15, device 200 has an overall length of about 0.54 inches and has a maximum diameter of about 0.125 inches.

According to aspects of the invention, clog-resistant fluid orifices may be formed between a passively movable component and a device housing, wherein the movable component is not part of a valve or other structure. In some embodiments, components forming an orifice, such as a movable component and a housing, may comprise dissimilar metals. The dissimilar metals can create an electrical potential between the components that changes the hydrophobicity of the surface(s). This in turn can repel proteins and or inhibit tissue ingrowth. In some embodiments, the electrical potential is tuned to attract particular biomarkers that the device is configured to sample.

According to aspects of the invention, the exemplary fluid interface devices disclosed herein can be used in various applications. For example, the devices may be used in hydrocephalus drainage systems (such as for brain injuries), in hemodialysis systems, in fluid sampling systems, in wound care (such as for Extremity Compartment Syndrome, reconstructive flaps, burns, surgical incisions, etc.) The devices may also be used for drug delivery, such as long-term chemotherapeutics, localized drug delivery to tumor sites, delivery of antibiotics, pain medications, regenerative growth factors, etc. In some applications such as hydrocephalus drainage systems, typical fluid flow rates can be around 2 milliliters per minute or less. In other applications, fluid flow rates may be about 40 ml/min. unassisted and 400 ml/min. under assistance, such as suction or pressure.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. An implantable occlusion resistant fluid interface comprising:

an outer housing formed from at least one biocompatible material and configured without sharp external edges or corners, the outer housing at least partially defining an internal housing cavity;

an orifice member formed from at least one biocompatible material and coupled with the outer housing in a manner that permits the orifice member to be freely movable in at least one of a lateral direction and a longitudinal direction with respect to the outer housing and to float between a first side and an opposite side of the outer housing, the movable orifice member together with the first side of the outer housing at least partially defining edges of a first orifice, the first orifice providing fluid communication between the internal housing cavity and an exterior of the outer housing, the first orifice having a first elongated cross-section configured to be transverse to a fluid flow between the internal housing cavity and the exterior of the outer housing, the first elongated cross-section having a maximum width and configured with a length that is at least four times the maximum width, wherein the maximum width of the first elongated cross-section varies when the orifice member floats or moves with respect to the outer housing, wherein the first orifice is configured to be in direct fluid contact with a region of a patient without an intervening restriction located between the first orifice and the region of the patient, the movable orifice member together with the opposite side of the outer housing at least partially defining edges of a second orifice, the second orifice providing fluid communication between the internal housing cavity and the exterior of the outer housing, the second orifice having a second elongated cross-section configured to be transverse to a second fluid flow between the internal housing cavity and the exterior of the outer housing, the second elongated cross-section having a second maximum width and configured with a second length that is at least four times the second maximum width, wherein the maximum width of the second elongated cross-section varies when the orifice member floats or moves with respect to the outer housing, wherein the second orifice is configured to be in direct fluid contact with a second region of the patient without an intervening restriction located between the second orifice and the second region of the patient; and a catheter port located on the outer housing and configured to couple with a catheter such that the internal housing cavity is in fluid communication with a lumen of the catheter when coupled to the catheter port.

2. The fluid interface of claim 1, wherein the maximum width of the transverse cross-section of the first orifice does not exceed 0.003 inches.

3. The fluid interface of claim 1, wherein the orifice member is freely movable in both the lateral direction and the longitudinal direction with respect to the outer housing.

4. The fluid interface of claim 3, wherein the movable orifice member comprises a plate.

5. The fluid interface of claim 1, wherein the housing is formed from at least two separate pieces that are joined together to captivate the orifice member therebetween.

6. The fluid interface of claim 5, wherein each of the at least two separate pieces is an elongated hemispherical toroidal shell that form a completed elongated toroidal shell when joined together, and wherein the orifice member is located across a central aperture of the toroid.

7. The fluid interface of claim 1, wherein the first and the second elongated cross-sections have a combined width that remains constant as the orifice member floats between the first side and the opposite side of the outer housing such that fluid flow through the fluid interface is not restricted as the orifice member floats.

8. The fluid interface of claim 7, wherein the first and the second elongated cross-sections have a combined width that remains constant as the orifice member freely moves in at least one of a lateral direction and a longitudinal direction with respect to the outer housing such that fluid flow through the fluid interface is not restricted as the orifice member freely moves.

9. The fluid interface of claim 1, wherein the orifice member movably resides in an oval shaped aperture through the outer housing.

10. An implantable occlusion resistant fluid interface comprising:
   a housing formed from at least one biocompatible material and configured without sharp external edges or corners, the housing at least partially defining an internal housing cavity;
   an orifice member formed from at least one biocompatible material and at least partially defining an orifice between the internal housing cavity and an exterior of the housing, the orifice having an elongated transverse cross-section configured to be transverse to a fluid flow between the internal housing cavity and the exterior of the housing, the elongated cross-section having a maximum width and configured with a length that is at least four times the maximum width, wherein the orifice is configured to be in direct fluid contact with a region of a patient without an intervening restriction located between the orifice and the region of the patient; and
   a catheter port located on the housing and configured to couple with a catheter such that the internal housing cavity is in fluid communication with a lumen of the catheter when coupled to the catheter port,
   wherein the orifice member comprises nano-ripples formed by ion blasting on one or more surfaces, the nano-ripples having a height of 50 nm or less and a spacing of 52 nm or less.

11. An implantable occlusion resistant shunt comprising: the fluid interface of claim 1; and
   a flexible catheter formed from a biocompatible material and having a first end and a second end, wherein the first end is coupled with the catheter port of the fluid interface.

12. The shunt of claim 11, further comprising a second fluid interface according to claim 1, wherein the second end of the catheter is coupled with the catheter port of the second fluid interface.

13. A method of treating hydrocephalus comprising:
   providing the shunt of claim 11;
   implanting the fluid interface and the first end of the catheter within a patient adjacent to brain tissue;
   implanting a remainder of the catheter within the patient; and
   locating the second end of the catheter in a region of the patient away from the brain tissue.

* * * * *